United States Patent [19]
Lipton

[11] Patent Number: 5,334,618
[45] Date of Patent: Aug. 2, 1994

[54] METHOD OF PREVENTING NMDA RECEPTOR-MEDIATED NEURONAL DAMAGE

[75] Inventor: Stuart A. Lipton, Newton, Mass.

[73] Assignee: The Children's Medical Center Corporation, Boston, Mass.

[21] Appl. No.: 939,824

[22] Filed: Sep. 3, 1992

Related U.S. Application Data

[63] Continuation-in-part of Ser. No. 680,201, Apr. 4, 1991, abandoned.

[51] Int. Cl.$^5$ .............................................. A61K 31/13
[52] U.S. Cl. ................................ 514/659; 514/662
[58] Field of Search ............................... 514/659, 662

[56] References Cited

U.S. PATENT DOCUMENTS

| | | |
|---|---|---|
| 3,328,251 | 6/1967 | Smith . |
| 3,391,142 | 7/1968 | Mills . |
| 3,456,057 | 7/1969 | Cairns et al. .................. 424/325 |
| 4,122,193 | 10/1978 | Scherm . |
| 4,148,896 | 4/1979 | Smith et al. .................. 424/248.56 |
| 4,351,847 | 9/1982 | Griffith et al. .................. 424/325 |
| 4,806,543 | 2/1989 | Choi . |
| 4,837,218 | 6/1989 | Olney .................................. 514/646 |
| 5,061,703 | 10/1991 | Bormann et al. .................. 514/212 |

FOREIGN PATENT DOCUMENTS 0002065 5/1979 European Pat. Off. ...... A61K 31/15

OTHER PUBLICATIONS

Asanaka et al, 112CA:232458q, 1990.
Merck Index 10th Ed #A7, 8116 & 373, 1988.
Turski, Arzneim-Forsch./Drug Res. 40(I). Nr.5 (1990) p. 511.
Meldrum et al., Trends in Parm. Sciences 11:379–387 (1990).
Rothman et al., Trends in Neurosci. 10:299–302 (1987).
Kornhuber et al., Eur. J. Pharm. 166:589–590 (1989).
Bormann, Eur. J. Pharm. 166:591–592 (1989).
Braunwald et al., Principles of Internal Med. 11th Ed. (N.Y. McGraw Hill 1987) pp. 1392–1396 & 2017–2019.
Hahn et al., Proc. Nat'l. Acad. Sci. USA 85:6556–6560 (1988).
Choi et al., Neuron 1:623–634 (1988).

*Primary Examiner*—Marianne M. Cintins
*Assistant Examiner*—Russell Travers
*Attorney, Agent, or Firm*—Fish & Richardson

[57] ABSTRACT

Disclosed is a method for reducing non-ischemic NMDA receptor-mediated neuronal damage in a mammal by administering to the mammal a compound of the formula shown in FIG. 1 (or a physiologically-acceptable salt thereof), wherein $R_1$ includes an amino group, $R_2$–$R_{17}$ are independently H or a short chain aliphatic group comprising 1–5 carbons, and $R_4$ and $R_{10}$ also may (independently) be a halogen or an acyl group. Also disclosed is a screen for antagonists of NMDA receptor mediated neurotoxicity which have an enhanced prospect for being clinically tolerated and selective against such neurotoxicity.

14 Claims, 3 Drawing Sheets

METHOD OF PREVENTING NMDA RECEPTOR-MEDIATED NEURONAL DAMAGE

BACKGROUND OF THE INVENTION

This application is a continuation-in-part of my earlier co-pending commonly owned application, U.S. Ser. No. 07/680,201, now abandoned filed Apr. 4, 1991.

This invention relates to the therapies using the substance amantadine and related compounds particularly memantine and rimantidine.

Amantadine and/or related compounds have been proposed for various therapies. Initially, these compounds were proposed to treat influenza virus. For example, Mills et al. U.S. Pat. No. 3,391,142 discloses adamantylamines which are said to be antiviral agents. Griffin U.S. Pat. No. 4,351,847 discloses that an amantadine derivative is effective against herpes simplex virus. Smith U. S. 3,328,251 discloses (at 13:24-31) that certain amantadine related compounds are effective against animal viruses, particularly swine influenza.

By chance, it was also observed that amantadine and related compounds are effective against the symptoms of Parkinson's disease. Tominack and Hayden (pp.460-461). See also, Scherm U.S. Pat. No. 4,122,193 at 6:54-60. Braunwald et al. (Principles of Internal Medicine, 11th ed., p. 2017, New York, McGraw Hill, 1987) report that amantadine has been used to treat Parkinson's disease and that its effect is achieved by its capacity to release stored dopamine from presynaptic terminals. See also Merk Index, p.55, #373; p. 1188, #8116; and APP-2, #A7, disclosing the use of various compounds for influenza A, treatment of Parkinsonism, and drug-induced extrapyramidal reactions; one such compound is reportedly being studied in control of micturition and limb muscle mobility, as well as an antispasmodic.

Other uses for such compounds have been proposed. For example, Scherm '193 (at 6:56–60) discloses that certain compounds can be used for treating "other kinds of hyperkinesis [in addition to Parkinsonism] including head tremors, thalamic tension conditions and spastic conditions, and even for the activation of akinetic cerebroorganic conditions."

Bormann et al. U.S. Pat. No. 5,061,703 discloses certain amantadine derivatives are useful not only for the treatment of parkinsonian and parkinsonoid diseases, by a mode of action attributed to a dopaminergic influence on the central nervous system (2:38-3:17), but also to reduce neuronal damage associated with cerebral ischemia, which is mediated by the N-methyl-D-aspartate (NMDA) subtype of excitatory amino acid receptor. Bormann et al. reports that certain adamantine derivatives ". . . exhibit NMDA receptor channel-antagonistic and anticonvulsive properties." (2:61-63 ). It also reports (3:10-16) that the adamantine derivatives "are especially suited for the prevention and treatment of cerebral ischemia after apoplexy, open-heart surgery, cardiac standstill, subarachnoidal hemorrhage, transient cerebro-ischemic attacks, perinatal asphyxia, anoxia, hypoglycemia, apnoea and Alzheimer's disease. [Emphasis added.]"

Turski et al. (Nature 349:414, 1991), reports certain experiments investigating the role of excitatory amino acids in dopaminergic toxicity caused by intake of a toxin known as MPTP (1-methyl-4-phenyl-1,2,3,6,-tetra hydropyridine). Excitatory amino acid antagonists were coadministered with MPP+ (the active metabolite of MPTP), and certain NMDA antagonists offered temporary protection against MPP+.

Meldrum, Trends Pharm. Sci. September, 1990, vol. 11, pp. 379-387 reviews reported literature concerning the possibility that excitatory amino acid receptor agonists of endogenous or environmental origin contribute to neuronal degeneration in disease states. After reviewing the several known receptors implicated in excitatory amino acid activity (particularly glutamate activity), the authors review (p. 386) suggestions that excitotoxic mechanisms might play a role in the pathogenesis of various chronic neurodegenerative disorders including Huntington's disease, olivo-pontocerebellar atrophy, senile dementia of the Alzheimer type, parkinsonism and amyotrophic lateral sclerosis (ALS), as well as two chronic syndromes linked to plant toxins.

Rothman et al. Trends Neurosci. 10:299-302 (1987) also review literature concerning the possibility that glutamate neurotoxicity may be responsible for neuronal degeneration in various neurological disorders.

Bormann, Eur. J. Pharm. (1989) 166:591-592 reports that memantine blocks NMDA receptor channels.

Kornhuber et al. Eur. J. Pharm. 166:589-590 (1989) report that memantine inhibits the binding of an NMDA antagonist (K-801) to post-mortem human brain homogenates.

Hahn et al. Proc. Nat'l Acad. Sci. (1988) 85:6556-6560 report that it is widely held that a glutamate-like toxin that resembles NMDA may be responsible for the death of nerve cells seen after severe neurological insults including stroke, seizures, and degenerative disorders, such as Huntington's disease, Alzheimer's disease, and the amyotrophic lateral sclerosis-parkinsonism-dementia complex found on Guam. They report findings suggesting that $Ca^{++}$ entry through NMDA-activated channels is responsible for this type of neuronal death and suggest strategies that may be clinically useful in the treatment of various neurological disorders.

Choi, Neuron 1:623-634 report that neurotoxicity due to excitatory amino acids may be involved in slowly progressive degenerative diseases such as Huntington's disease.

SUMMARY OF THE INVENTION

In general, the invention features a method which, in contrast to Bormann '703, cited above, reduces receptor-mediated neuronal degeneration in a mammal in disease states which are non-ischemic. The method involves administering to the mammal a compound of the formula shown in FIG. 1 (or a physiologically acceptable salt thereof) wherein $R_1$ includes an amino group, and $R_2$-$R_{17}$ are independently H or a short chain aliphatic group including 1-5 carbons, and $R_4$ and $R_{10}$ (independently) may also be a halogen (particularly fluorine, chlorine or bromine) or an acyl group. The compound is administered in a concentration effective to cause such reduction in neuronal degeneration.

In preferred embodiments, $R_1$ is $NH_2$, and the compound is preferably amantadine; $R_4$ is a methyl group; $R_{10}$ is a methyl group; $R_4$ and $R_{10}$ are both methyl groups; $R_4$ and $R_{10}$ are both methyl groups and $R_1$ is $NH_2$, and the compound is preferably memantine.

Alternatively, $R_1$ may be

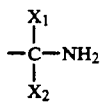

wherein $X_1$ and $X_2$ are independently H or a short chain aliphatic group including between 1-5 carbons [i.e., either a methyl group or between 1-4 (—$CH_2$) groups and a terminal methyl group]; $R_4$ is a methyl group; $R_{10}$ is a methyl group; $R_4$ and $R_{10}$ are methyl groups; $X_1$ and $X_2$ are H and $CH_3$, respectively, or $X_1$ and $X_2$ are $CH_3$ and H, respectively; and the compound is preferably rimantadine.

In various other preferred embodiments, the mammal is a human infected with a human immunodeficiency virus; the human manifests symptoms of the AIDS related complex or acquired immunodeficiency syndrome; the neurotoxicity is mediated (directly or indirectly) by an excitatory amino acid, or a structurally similar compound such as quinolinate, which leads to the activation of an NMDA receptor-operated ionic channel; for example, the neurotoxicity is mediated by glutamate, aspartate, homocysteic acid, cysteine sulphinic acid, cysteic acid, quinolinate, or N-acetyl aspartyl glutamate.

By "non-ischemic, long-term NMDA receptor-mediated neuronal degeneration" is meant progressive neuronal injury over a long period of time as a result of stimulation or costimulation of the NMDA receptor. In particular, I mean to include the neurodegeneration associated with long term disease states such as Huntington's disease, Alzheimer's disease, amyotrophic lateral sclerosis (ALS, which is also known as motor neuron disease), acquired immunodeficiency (AIDS). Other conditions that may be treated in accordance with the invention include: neurolathyrism (resulting from β-N-oxalyamino-L-alanine found in chick peas); "Guam disease" (resulting from β-N-methyl-amino-L--alanine found in flour from cycad seeds); and olivo-pontocerebellar atrophy. The invention also includes therapies for certain mitochondrial abnormalties or inherited biochemical disorders including: MELAS syndrome (mitochondrial myopathy, encephalopathy, lactic acidosis and stroke-like episodes); Rett syndrome; homocysteinuria; hyperprolinemia; hyperglycinemia (non-ketotic); hepatic encephalopathy; uremic encephalopathy; and 4-hydroxybuturic aciduria. The invention also includes treating peripheral neuropathy, especially painful types of peripheral neuropathy which may be of central nervous system origin. The invention also includes treating certain acute conditions including trauma (e.g., spinal, brain or eye trauma) carbon monoxide poisoning; lead poisoning; or domoic acid poisoning (domoic acid is a glutamate-like agonist found in contaminated muscles).

Useful compounds of the instant invention include a tricyclic 10 carbon ring which includes at least one amino group at position $R_1$ of the general formula shown in FIG. 1. The amino group may be attached directly to a ring carbon (as is the case for amantadine; see FIG. 2a), or it may be attached to a carbon attached to the carbon ring (as is the case for rimantadine; see FIG. 2b). $R_2$–$R_{17}$ (of the general formula of FIG. 1) are hydrogen atoms, methyl groups, or short chain aliphatic groups which include between 1-5 saturated carbons (i.e., 1-4 (—$CH_2$) groups and a terminal methyl group], or any combination, thereof. The neuroprotective potency of the compounds may be enhanced by substitutions of ring hydrogens. In one example, methyl group substituants at positions $R_4$ and $R_{10}$ (of the general formula shown in FIG. 1) greatly enhance the ability and potency of the compound, memantine (shown in FIG. 2c), to prevent glutamate-induced neuronal damage. Memantine is neuroprotective in vitro at a concentration of 2-12 μM (see below); amantadine, a molecule unsubstituted at these positions, is effective at a concentration of approximately 200μM. The water solubility of compounds of the general formula shown in FIG. 1 may be increased by formulating the compound into a physiologically-acceptable salt, e.g., by reaction with HCl.

The preferred compounds of the invention (i.e., amantadine, rimantadine, and memantine, and similar derivatives) are water soluble and are able to pass readily through the blood brain barrier, facilitating a therapy which is both extremely rapid and unusually potent. The preferred compounds also provide the advantage of a proven record of safe human administration (i.e., for treatment of viral infections or for treatment of Parkinson's disease, but not neuronal degeneration of Parkinsonism). For example, amantadine has been approved for use by human patients, at least, in the United States. Disorders which may be treated by the method of the invention are listed above in this application.

Another aspect of the invention features methods of screening compounds to identify those with an increased prospect for safety and efficacy, by selecting NMDA receptor channel complex antagonists characterized in that they operate quickly and quickly cease operation after administration of the compound ceases, and in that they require the presence of an NMDA-excitatory compound in order to block activity. According to this second aspect of the invention candidate NMDA channel antagonists are preliminarily screened for safety and efficacy by: (a) assessing the time period required for the candidate to induce blockade of NMDA-receptor-associate ion channels; (b) assessing the time period required for loss of blockade of ion channels when administration of the compound ceases; and (c) assessing the ability of the compound to block NMDA mediated current in the absence of an NMDA-excitatory compound. Compounds selected are those with time periods (a) and (b) that are shorter than the time periods characteristic of MK-801 and with a substantially negative result in step (c), above, thereby enhancing the prospect that the candidate will be a clinically tolerated selective NMDA antagonist. Those compounds are then tested to verify that they protect against NMDA mediated neurotoxicity.

Other features and advantages of the invention will be apparent from the following detailed description and from the claims.

BRIEF DESCRIPTION OF THE DRAWINGS

Drawings

The present invention is based on the finding that the amantadine derivative memantine (1-amino-3,5-dimethyl adamantine) reduces neuronal damage (see below); and that this reduction in damage is due to a block of NMDA receptor-operated channel activation by excitatory amino acids (such as glutamate-related compounds) using concentrations of memantine that are readily obtainable in human patients taking the drug (Wesemann et al., J. Neural Transmission (Supp.) 16:143, 1980). An increased level of one or more glutamate-related compounds is associated with many neurodegenerative disorders (e.g., those listed above), and amantadine derivatives are therefore useful for their treatment. In addition to glutamate itself, neuronal injury may result from stimulation of the NMDA receptor by other excitatory amino acids or structurally similar compounds; examples of such compounds are aspartate, homocysteic acid, cysteine sulphinic acid, cysteic acid, and quinolinate. Neuronal injury may also result from stimulation by excitatory peptides, such as N-acetyl aspartyl glutamate.

Other compounds structurally related to memantine are also preferred for use in the invention. By "structurally related" is meant a compound composed of a tricyclic 10 carbon ring bearing an amino group. Such compounds include, but are not limited to, amantadine (1-adamantanamine hydrochloride) itself and rimantadine (alpha-methyl-1-adamantanemethylamine hydrochloride).

Figure 1:
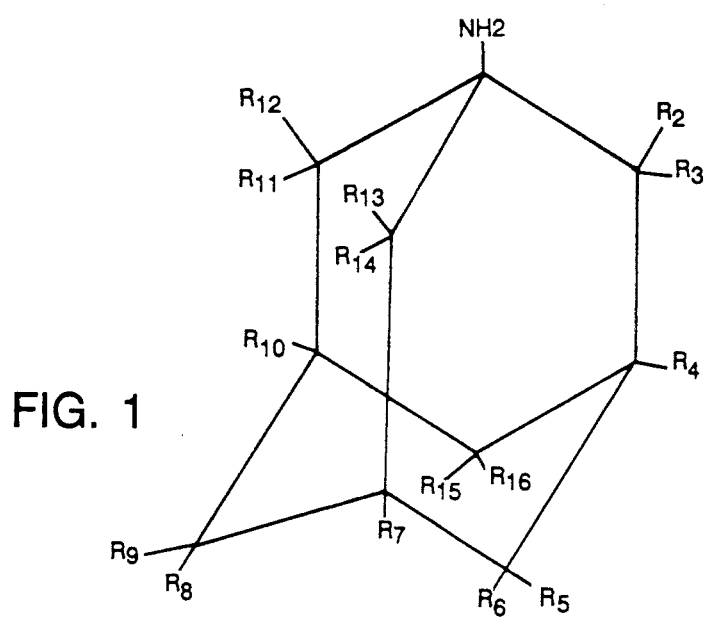
FIG. 1 is the general formula of the compounds useful in the method of the invention.
Figure 2A:
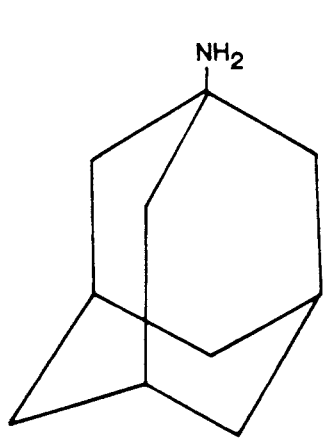
FIG. 2 is a schematic representation of (a) amantadine, (b) rimantadine, and (c) memantine.
Figure 2B:
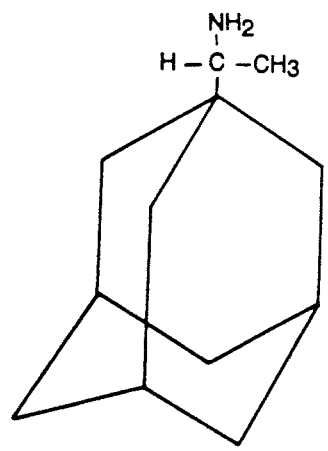
Figure 2C:
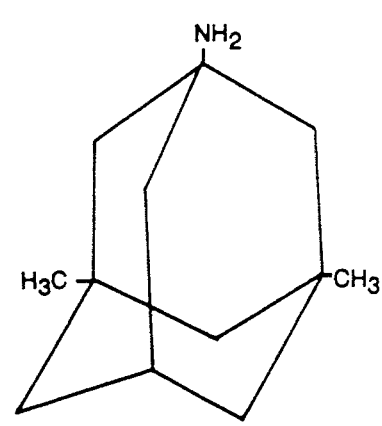

Compounds of the invention (i.e., those of the general formula shown in FIG. 1 and including compounds bearing substitutions predicted to increase potency) may be tested for efficacy in reducing neuronal damage using the assay described below; an effective compound will cause a decrease in neuronal cell death. Compounds most preferred in the invention are those which effect the greatest protection of neurons from NMDA receptor-mediated injury, e.g., that injury resulting from stimulation of the NMDA receptor by glutamate (as shown below) or other excitatory amino acids or structurally similar compounds or from stimulation by excitatory peptides, such as N-acetyl aspartyl glutamate.

Assay for Neuronal Cell Function and Death

To test amantadine derivatives for their ability to prevent neurotoxicity, neuronal cell death may be assayed as follows. Under general anesthesia, the fluorescent dye granular blue (Mackromolecular Chemin, Umstadt, FRG) is injected as approximately a 2% (w/v) suspension in saline into the superior colliculus of 4- to 6-day-old Long–Evans rats (Charles River Laboratory, Wilmington, MA). Two to 6 days later, the animals are sacrificed by decapitation and enucleated, and the retinas quickly removed. The retinas are dissociated by mild treatment with the enzyme papain and cultured in Eagle's minimum essential medium (MEM, catalog #1090, Gibco, Grand Island, N.Y.) supplemented with 0.7% (w/v) methylcellulose, 0.3% (w/v) glucose, 2 mM glutamine, 1 μg/ml gentamicin, and 5% (v/v) rat serum, as described in Lipton et al., J. Physiol. 385:361, 1987. The cells are plated onto 75 mm$^2$ glass coverslips coated with poly-L-lysine in 35 mm tissue culture dishes. The candidate amantadine derivative is added (e.g., in a series of concentrations ranging from 1 nM - 1 mM) in the presence or absence of compounds which activate the NMDA receptor-operated channel complex, and in high calcium, low magnesium medium (10 mM $CaCl_2$, 50 μM $MgCl_2$) to enhance NMDA-receptor neurotoxicity in this preparation (Hahn et al., Proc. Natl. Acad. Sci. USA 85:6556, 1988; Levy et al., Neurology 40:852, 1990; Levy et al., Neurosci. Lett. 110:291, 1990). The degree of survival (under these ionic conditions or with added exogenous NMDA (200 μM))is compared to that in normal medium (1.8 mM $CaCl_2$, 0.8 mM $MgCl_2$), which minimizes NMDA receptor-mediated injury in this preparation (Hahn et al., cited above). Incubations last 16–24 h at 37° C. in an atmosphere of 5% $CO_2$/95% air. The ability of retinal ganglion cells to take up and cleave fluorescein diacetate to fluorescein is used as an index of their viability as described in detail in Hahn et al. (Proc. Natl. Acad. Sci. USA 85:6556, 1988). Dye uptake and cleavage generally correlate well with normal electrophysiological properties assayed with patch electrodes.

To perform the viability test, the cell-culture medium is exchanged for physiological saline containing 0.0005% fluorescein diacetate for 15–45 s, and then cells are rinsed in saline. Retinal ganglion cell neurons that do not contain the fluorescein dye (and thus are not living) often remain visible under both phase-contrast and UV fluorescence optics, the latter because of the continued presence of the marker dye granular blue; other dead retinal ganglion cells disintegrate, leaving only cell debris. In contrast, the viable retinal ganglion cells display not only a blue color in the UV light but also a yellow-green fluorescence with filters appropriate for fluorescein. Thus, the use of two exchangeable fluorescence filter sets permits the rapid determination of viable ganglion cells in the cultures. The ganglion cells are often found as solitary neurons as well as neurons lying among other cells in small clusters.

An amantadine derivative may be tested for utility in the method of the invention using any type of neuronal cell from the central nervous system, as long as the cell can be isolated intact by conventional techniques. In addition to the retinal cultures described above, we have also used hippocampal and cortical neurons, but any neuron can be used that possess NMDA receptors (e.g., neurons from other regions of the brain). Such neurons may be prenatal or postnatal, and they may be from a human, rodent or other mammals. In one example, retinal cultures can be produced from postnatal mammals; they are well-characterized and contain a central neuron, the retinal ganglion cell, that can be unequivocally identified with fluorescent labels. A substantial portion of retinal ganglion cells in culture display both functional synaptic activity and bear many, if not all, of the neurotransmitter receptors found in the intact central nervous system.

There now follows an example of an amantadine derivative useful in the method of the invention and an illustration of its efficacy in reducing neuronal damage. This example is provided to illustrate the invention and should not be construed as limiting.

Memantine Prevents NMDA Receptor-Mediated Neurotoxicity

Using the assay described above, the amantadine derivative, memantine, was tested for its ability to increase survival of glutamate-treated retinal ganglion cells. In eight separate experiments, retinal ganglion cells were cultured in either normal medium (i.e., MEM containing 1.8 mM $CaCl_2$, 0.8 mM $MgCl_2$) or in high calcium, low magnesium medium (i.e., 10 mM $CaCl_2$, 50 μm $MgCl_2$). The latter medium is known to enhance NMDA receptor-mediated neurotoxicity due to an endogenous glutamate receptor agonist (Hahn et al., Proc. Natl. Acad. Sci. USA 85:6556, 1988; Levy et al., Neurology 40:852, 1990; Levy et al., Neurosci. Lett. 110:291, 1990). Memantine HCl was diluted in double-distilled water, filtered, and added to the growth media (to a final concentration of between 1 μM-25μM). The retinal cells were incubated for 16–20 hours at 37° C. in a humidified atmosphere of 5% $CO_2$ and 95% air.

Figure 3:
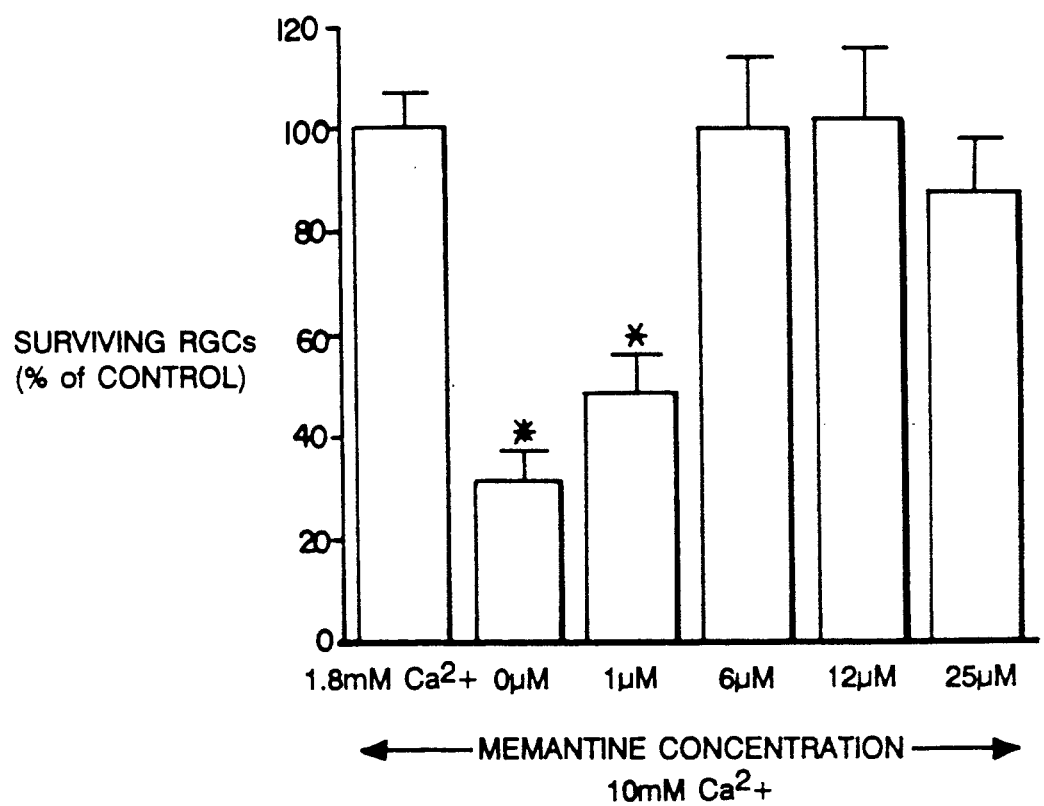
FIG. 3 is a graphical representation showing that memantine prevents glutamate-mediated retinal ganglion cell neurotoxicity.

As shown in FIG. 3, an endogenous-glutamate-like agonist produces retinal cell neurotoxicity in the presence of elevated extracellular calcium concentrations (compare FIG. 3, columns 1 and 2). To verify that the agonist was glutamate-related, the enzyme glutamate-pyruvate transaminase (GPT; 0.25 mg/ml; Boehringer-Mannheim, Indianapolis, IN) was added; this enzyme specifically degrades endogenous glutamate by transaminating it to α-keto-glutamate in the presence of pyruvate. Under these conditions, survival of retinal ganglion cells was enhanced; i.e., an approximately equal number of neurons survived in the high calcium, low magnesium medium plus GPT and pyruvate (2 mM) as survived in the control cultures in normal medium. This finding indicated that the endogenous toxin was glutamate itself. HPLC analysis verified the breakdown of glutamate by GPT.

The amantadine derivative, memantine, prevented retinal ganglion cell death from the endogenous glutamate-related toxin in a dose-dependent manner (FIG. 3). Increased neuronal survival at 6 μM memantine (FIG. 3, column 4) reached statistical significance compared to the control (FIG. 3, column 1). All experiments depicted in FIG. 3 involving memantine treatment were repeated in triplicate and normalized to control cultures (i.e., normal medium lacking memantine). The values depicted represent mean +standard error of the mean (SEM). An analysis of variance was used to test for significance; this analysis was followed by a Scheffé test for multiple comparison of means (Hahn et al., 1988, supra).

These data indicate that memantine blocks neuronal cell death mediated by excessive stimulation of the NMDA receptor. Without being bound to any theory as to the mechanism whereby memantine exerts its neuroprotective effect, it is possible that memantine blocks the glutamate-induced increase in intracellular $Ca^{2+}$ at the NMDA receptor-associated ionic channel. By analogy with MK-801 (dizocilpine; an NMDA-specific antagonist), the mode of action of memantine may be an un-competitive inhibition of $Ca^{2+}$ influx by blocking the NMDA receptor-operated channels. If so, inhibition by memantine is contingent upon prior activation of the receptor by the agonist. This has important consequences at the therapeutic level. Normal NMDA receptor activation (for example, that involved in long-term potentiation, a form of learning and memory) may be unaffected by the compounds of the invention while neuronal injury resulting from escalating levels of glutamate or other excitatory compounds might be effectively blocked (Karschin et al., J. Neurosci. 2895, 1988; Levy and Lipton, Neurology 40:852, 1990). Memantine analogs have undergone clinical trials in the United States and in the Soviet Union using therapeutic doses for influenza A therapy. Those studies revealed only limited and reversible central nervous system side effects (Tominack et al., Infect. Dis. Clin. N. Am. : (2) :459, 1987; Clover et al., Am. J. Dis. Child. 140:706, 1986; Hall et al., Pediatrics 80(2) :275, 1987; Zlydnikov et al, Reviews of Infect. Dis. (3) :408, 1981; Dolin et al, New Eng. J. Med. 302:580, 1982). There has been one case report of visual loss in an adult patient who had been treated for Parkinson's symptoms with amantadine for several weeks. However, full visual acuity returned after drug discontinuation (Perlman et al., JAMA 237:1200, 1977).

In selecting other NMDA channel complex blockers within the scope of the above invention, it is important to understand the implications of the above memantine data. First, it is useful to select an uncompetitive NMDA inhibitor—i.e., one whose inhibitory activity is contingent on prior activation of the receptor by a receptor agonist. Second, it is useful to select NMDA inhibitors that operate quickly and are quickly reversed upon cessation of administration of the drug. This strategy maximizes normal CNS function and reduces side effects.

As shown by the following examples memantine's kinetics for blocking/unblocking NMDA receptor-mediated response are relatively rapid.

Figure 4A:
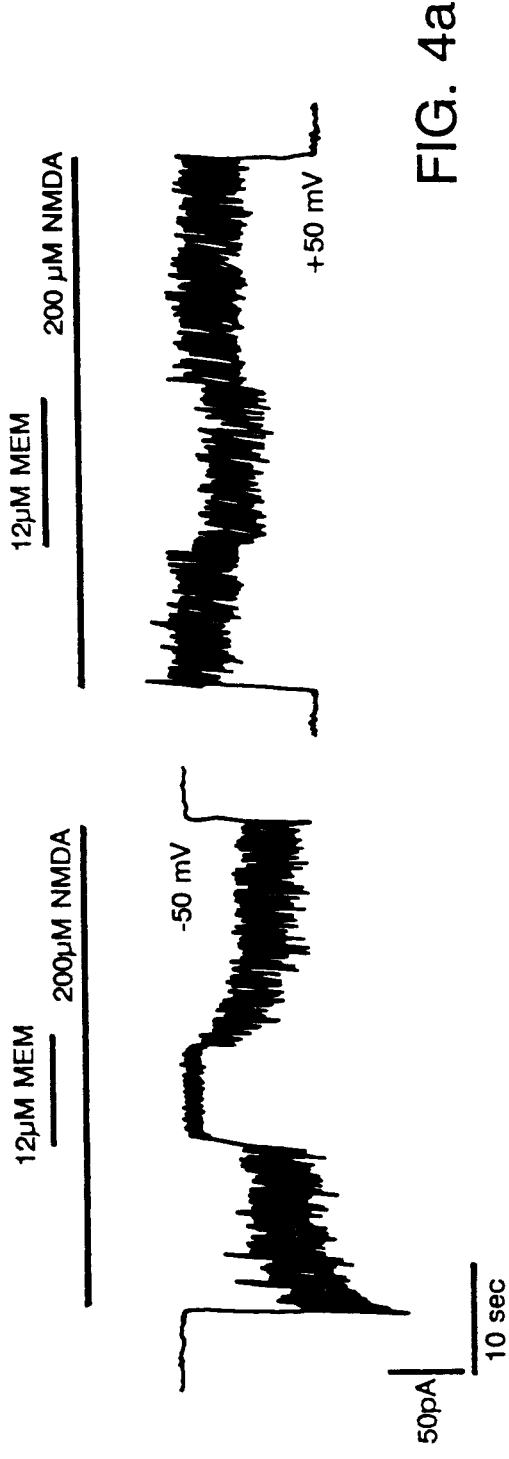
FIGS. 4A–4B are representations of results of patch clamp experiments described below.
Figure 4B:
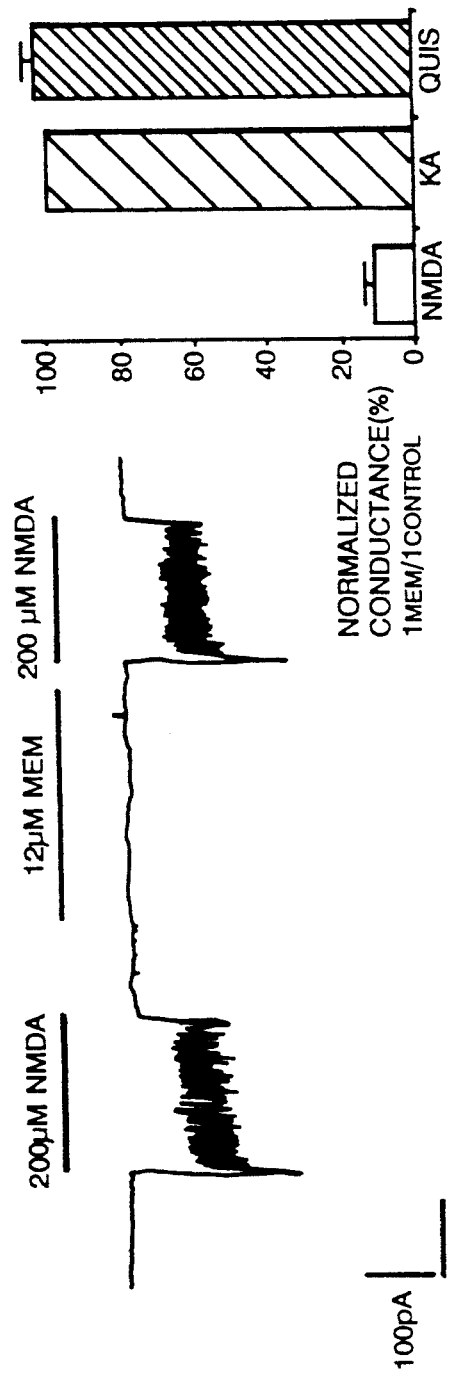

FIG. 4 depicts evidence for open-channel block of NMDA-elicited whole-cell current by memantine (MEM) on rat retinal ganglion cells. FIG. 4A shows a blocking effect of 12 μM memantine on 200 μM NMDA-induced current at holding potentials of −50 and +50 mV in whole-cell recordings. FIG. 4B shows a lack of effect on 200 μM NMDA-induced current of 12 μM memantine when administered alone at −60 mV (left). When coapplied with agonist, 12 μM memantine did not affect the current elicited by 50 μM kainate (KA) or 5 μM quisqualate (QUIS), whereas the response to 200 μM NMDA was inhibited by 90% at −60 mV (n=17) (right). A rapid application system was used to administer the drugs, and a fast washout method was used in the experiments shown in FIGS. 4A and 4B.

The above experiments were performed as follows.

Cell Culture

For retinal ganglion cell labeling, dissociation, and culture, we used techniques that have been detailed elsewhere (Leifer et al. (1984) Science 224:303–306). Briefly, retinal ganglion cells of 4-6-d-old Long-Evans rats were retrogradely labeled with granular blue by injection in the superior colliculus and retrograde transport. Two to six days later, the animals were killed by decapitation. Following enucleation, the retinas were dissociated with mild treatment with the enzyme papain. The retinal cells were than plated onto glass coverslips coated with poly-L-lysine in 35 mm tissue culture dishes. The growth medium was Eagle's minimum essential medium supplemented with 0.7% (w/v) methylcellulose, 0.3% (w/v) glucose, 2 n4 glutamine, 5% (v/v) rat serum, and 1 μg/ml gentamicin. Retinal ganglion cells were identified by the presence of the retrogradely transported dye granular blue.

Patch-Clemp Electrophysiology

Whole-cell and single-channel recordings of rat retinal ganglion cells were performed as described in detail elsewhere (Hamill et al., 1981; Lipton and Tauck, 1987). The neurons were continuously superfused in a chamber at 27°–29° C. with a bath solution composed of (in mM) NaCl, 137.6; KCl, 5.8; $CaCl_2$, 2.5; HEPES, 5; glucose, 22.2; with phenol red, 0.001% (v/v); glycine, 1 μM; pH 7.2; and no added magnesium. The patch pipettes were filled with an intracellular solution containing (in mM) CsCl, 120; tetraethylammonium chloride, 20; HEPES, 10; EGTA, 2.25; CaCl₂, 1; and MgCl₂, 2; and sometimes with 3 mMMg-ATP to minimize rundown in prolonged recordings (pH 7.2). The agonists and antagonists were prepared in bath solution containing 1 mM tetrodotoxin (TTX), and they were applied by an array of pneumatic pipettes placed 20–50 μm from the neurons. Solution changes could be achieved rapidly, within 50–100 msec, by moving the array of constantly flowing pipette tips relative to the cell with a micromanipulator driver. A control pipette containing bath solution and 1 μM TTX was used to wash out NMDA-induced current rapidly.

Therapy

To prevent neuronal damage, amantadine and its derivatives may be administered by any of a number of routes in an amount sufficient to block glutamate's effect on the NMDA receptor. The amantadine derivative may be included in a pharmaceutical preparation, using a pharmaceutical carrier (e.g., physiological saline); the exact formulation of the therapeutic mixture depends upon the route of administration. Preferably, the compound is administered orally or intravenously, but it may also be administered intrathecally or intravitreally. The preferred compounds, amantadine, memantine, and rimantadine are administered at 100–500 μg/day, 5–80 mg/day, and 50–300 mg/day, respectively, in divided doses. Any other compound, determined to be an effective neuroprotective agent by the assays described herein, is administered orally, intravenously, intrathecally, or intravitreally at 100 μg–500 mg/day in divided doses. Treatment may be repeated as necessary to prevent or alleviate neurological injury. The compounds of the invention can be utilized to protect against slow progressive neurodegeneration associated with a number of disorders described above in this application.

The method of the invention is particularly preferred for the treatment of AIDS dementia and other neurological manifestations of the AIDS virus (HIV-1, HIV-2, and other forms of the virus). The method may also be used for reduction of neuronal damage resulting from infection with other viruses which cause damage to the nervous system. The invention also features treating acute and chronic neurodegenerative disorders described above.

Other Embodiments

The method described herein is useful for reducing neuronal injury in any mammal having NMDA receptors. Treatment of neuronal damage in humans is the preferred utility; but the method may also be employed successfully for veterinary purposes.

I claim:

1. A method of treating a patient to reduce painful peripheral neuropathy comprising administering to said patient a compound of the formula below, wherein $R_1$ comprises an amino group; $R_2$–$R_{17}$ are independently H or a short chain aliphatic group comprising 1–5 carbons; and $R_4$ and $R_{10}$ may also be a halogen or an acyl group, or a physiologically acceptable salt thereof, in a concentration effective to cause such reduction.

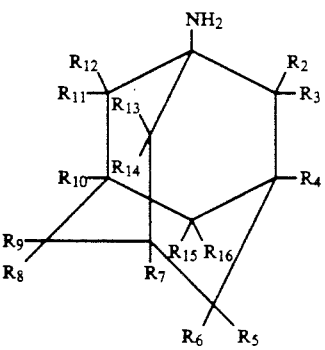

2. The method of claim 1, wherein $R_1$ is $NH_2$.
3. The method of claim 2, wherein said compound is amantadine.
4. The method of claims 1 or 2, wherein $R_4$ is a methyl group.
5. The method of claims 1 or 2, wherein $R_{10}$ is a methyl group.
6. The method of claim 1, wherein said $R_4$ and $R_{10}$ are methyl groups.
7. The method of claim 6, wherein said $R_1$ is $NH_2$.
8. The method of claim 7, wherein said compound is memantine.
9. The method of claim 1, wherein $R_1$ is

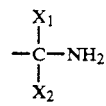

wherein $X_1$ and $X_2$ are independently H or a short chain aliphatic group comprising between 1–5 carbons.

10. The method of claim 9, wherein $X_1$ and $X_2$ are H and $CH_3$, respectively, or wherein $X_1$ and $X_2$ are $CH_3$ and H, respectively.
11. The method of claim 10, wherein said compound is rimantadine.
12. The method of claim 9, wherein $R_4$ is a methyl group.
13. The method of claim 9, wherein $R_{10}$ is a methyl group.
14. The method of claim 9, wherein $R_4$ and $R_{10}$ are methyl groups.

* * * * *

UNITED STATES PATENT AND TRADEMARK OFFICE
CERTIFICATE OF CORRECTION

PATENT NO. : 5,334,618

DATED : August 2, 1994

INVENTOR(S) : Stuart A. Lipton

It is certified that error appears in the above-identified patent and that said Letters Patent is hereby corrected as shown below:

```
Col. 7, line 68 after "Am." insert --1:--.
Col. 7, line 62, "2895" should be --8:2895--.
Col. 8, line 3, after "Dis." insert --3--.
Col. 8, line 55, "n4" should be --mM--..
Col. 8, line 59, "Clemp" should be --Clamp--.
```

Signed and Sealed this

Nineteenth Day of March, 1996

Attest:

BRUCE LEHMAN

*Attesting Officer*     Commissioner of Patents and Trademarks

UNITED STATES PATENT AND TRADEMARK OFFICE
CERTIFICATE OF CORRECTION

PATENT NO.    : 5,334,618
DATED         : AUGUST 2, 1994
INVENTOR(S)   : STUART A. LIPTON

It is certified that error appears in the above-identified patent and that said Letters Patent is hereby corrected as shown below:

At column 1, line 4, before "BACKGROUND OF THE INVENTION" insert --This invention was made with government support under Grant No. R01 EY09024 by the NIH. The government has certain rights in the invention.--

Signed and Sealed this

Nineteenth Day of September, 2000

Attest:

Q. TODD DICKINSON

Attesting Officer

Director of Patents and Trademarks